(12) United States Patent
Wolschek et al.

(10) Patent No.: US 11,339,377 B2
(45) Date of Patent: May 24, 2022

(54) SO3 CHROMATOGRAPHY FOR USE IN A METHOD FOR VIRUS PURIFICATION

(71) Applicants: Blue Sky Vaccines GmbH, Vienna (AT); BIA Separations D.O.O, Ljubljana (SI)

(72) Inventors: Markus Wolschek, Vienna (AT); Manfred Reiter, Vienna (AT); Ales Strancar, Ajdovscina (SI); Mojca Tajnik Sbaizero, Bagnaria Arsa (IT)

(73) Assignee: BLUESKY IMMUNOTHERAPIES GMBH, Vienna (AT)

( * ) Notice: Subject to any disclaimer, the term of this patent is extended or adjusted under 35 U.S.C. 154(b) by 0 days.

(21) Appl. No.: 16/762,119

(22) PCT Filed: Nov. 8, 2018

(86) PCT No.: PCT/EP2018/080571
§ 371 (c)(1),
(2) Date: May 6, 2020

(87) PCT Pub. No.: WO2019/092084
PCT Pub. Date: May 16, 2019

(65) Prior Publication Data
US 2020/0332264 A1 Oct. 22, 2020

(30) Foreign Application Priority Data
Nov. 8, 2017 (EP) ..................... 17200517

(51) Int. Cl.
| C07K 14/00 | (2006.01) |
| A61K 38/00 | (2006.01) |
| C07H 21/04 | (2006.01) |
| C07K 14/765 | (2006.01) |
| C12Q 1/68 | (2018.01) |
| C12N 7/00 | (2006.01) |

(52) U.S. Cl.
CPC ...... *C12N 7/00* (2013.01); *C12N 2760/16152* (2013.01); *C12N 2760/16252* (2013.01)

(58) Field of Classification Search
CPC .. C07K 14/765; C07K 2319/00; A61K 38/00; C12N 15/62; A61P 3/00
See application file for complete search history.

(56) References Cited

FOREIGN PATENT DOCUMENTS

| WO | 99/64068 A1 | 12/1999 |
| WO | 99/64571 A1 | 12/1999 |

OTHER PUBLICATIONS

Guo-jie et al., "Efficient clearance of herpes simplex virus using a GMP-compliant method for production of recombinant adeno-associated virus vectors", Molecular Therapy, 2015, 23(supplement 1):S186-S187.*
Zaveckas et al., "Purification of recombinant virus-like particles of porcine circovirus type 2 capsid protein using ion-exchange monolith chromatography", Journal of Chromatography B, 2015:21-28.*
Banjac et al., "Purification of Vero cell derived live replication deficient influenza A and B virus by ion exchange monolith chromatography", Vaccine, 2014, vol. 32, No. 1, pp. 2487-2492, http://dx.doi.org/10.1016/j.vaccine.2014.02.086.
Ferko et al., "Immunogenicity and Protection Efficacy of Replication-Deficient Influenza A Viruses with Altered NS1 Genes", J. Virol., 2004, vol. 78, No. 23, pp. 13037-13045, DOI: 10.1128/JVI.78.23.13037-13045.2004.
Ye et al., "Efficient Clearance of Herpes Simplex Virus Using a GMP-compliant Method for Production of Recombinant Adeno-associated Virus Vectors", AGTC, 2015, XP55460750, 1 page.
Kalashnikova et al., "Development of a Strategy of Influenza Virus Separation Based on Pseudoaffinity Chromatography on Short Monolithic Columns", Anal. Chem., 2008, vol. 80, No. 6, pp. 2188-2198, 0.1021/ac702258t.
Kalbfuss et al., "Purification of Cell Culture-Derived Human Influenza A Virus by Size-Exclusion and Anion-Exchange Chromatography", Biotech Bioeng., 2007, vol. 96, No. 5, pp. 932-944.
Kalbfuss et al., "Direct capture of influenza A virus from cell culture supernatant with Sartobind anion-exchange membrane adsorbers", J. Memb. Sci., 2007, vol. 299, pp. 251-260, doi:10.1016/j.memsci.2007.04.048.
Kramberger et al., "http://dx.doi.org/10.1016/j.vaccine.2014.02.086", J. Chromatogr. A, 2007, vol. 1144, No. 1, pp. 143-149, doi: 10.1016/j.chroma.2006.10.055.
Nayak et al., "Downstream processing of MDCK cell-derived equine influenza virus", J.Chromatogr. B Analyt Technol Biomed Life Sci, 2005; vol. 823, No. 2, pp. 75-81, doi:10.1016/j.jchromb.2005.05.022.
Opitz et al., "Lectin-affinity chromatography for downstream processing of MDCK cell culture derived human influenza A viruses", Vaccine, 2007, vol. 25, No. 5, pp. 939-947, doi:10.1016/j.vaccine.2006.08.043.
Optiz et al., "Sulfated Membrane Adsorbers for Economic Pseudo-Affinity Capture of Influenza Virus Particles", Biotechnol Bioeng., 2009, vol. 103, No. 6, pp. 1144-1154.
Strauss et al., "Anion Exchange Chromatography Provides a Robust, Predictable Process to Ensure Viral Safety of Biotechnology Products", Biotechnol. Bioengineering, 2009, vol. 102, No. 1, pp. 168-175.
Vicente et al., "Anion-exchange membrane chromatography for purification of rotavirus-like particles", J. Memb. Sci., 2008, vol. 311, pp. 270-283, doi:10.1016/j.memsci.2007.12.021.
Zaveckas et al., "Purification of recombinant virus-like particles of porcine circovirus type 2 capsid protein using ion-exchange monolith chromatography", J. Chromatogr. B, 2015, vol. 991, pp. 21-28.

(Continued)

*Primary Examiner* — Barry A Chestnut
(74) *Attorney, Agent, or Firm* — Loza & Loza, LLP; Michael F. Fedrick

(57) ABSTRACT

The present invention refers to a process for purifying virus particles from cell culture, comprising the steps of subjecting the cell culture to centrifugation to get a supernatant fraction of virus particles, incubating said fraction with a nuclease, diluting the fraction with low conductivity buffer, subjecting said diluted fraction to a SO3 chromatography step, performing a washing step with low conductivity buffer, and eluting virus particles.

19 Claims, 4 Drawing Sheets

(56) References Cited

OTHER PUBLICATIONS

Figure 1A:
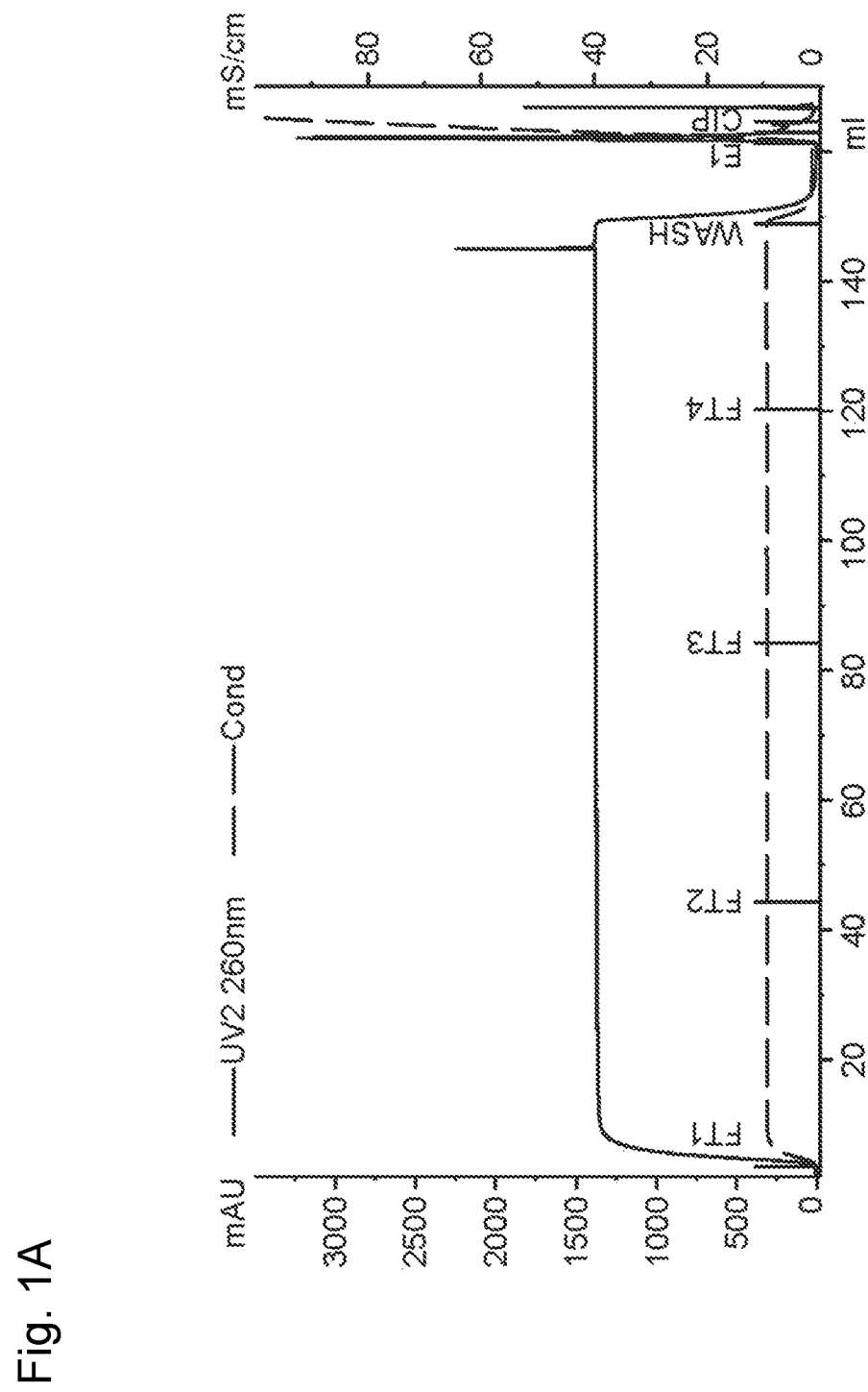

Extended European Search Report for EP17200517.5 dated Mar. 29, 2018; 6 pages.
International Search Report for PCT/EP18/80571 dated Dec. 19, 2018; 5 pages.
International Preliminary Report on Patentability for PCT/EP18/80571 dated May 12, 2020; 6 pages.

* cited by examiner

SO3 CHROMATOGRAPHY FOR USE IN A METHOD FOR VIRUS PURIFICATION

CROSS-REFERENCE TO RELATED APPLICATIONS

This application is the U.S. national stage of International Patent Application No. PCT/EP2018/080571, filed on Nov. 8, 2018 and entitled SO3 CHROMATOGRAPHY FOR USE IN A METHOD FOR VIRUS PURIFICATION, which claims the benefit of priority under 35 U.S.C. § 119 from European Patent Application No. 17200517.5, filed Nov. 8, 2018. The disclosures of the foregoing applications are incorporated herein by reference in their entirety.

FIELD OF THE INVENTION

The present invention refers to a process for purifying virus particles, specifically influenza virus particles, from cell culture, comprising the steps of subjecting the cell culture to centrifugation to get a supernatant fraction of virus particles, incubating said fraction with a nuclease, diluting the fraction with low conductivity buffer, subjecting said diluted fraction to a SO3 chromatography step, performing a washing step with low conductivity buffer, and eluting influenza virus particles.

BACKGROUND OF THE INVENTION

Harvests of viruses obtained from culturing on cell lines such as Vero cells contain not only the desired viruses but also proteins and DNA originating from the culture cells. However, when the viruses are intended for certain uses, such as the manufacture of vaccines, it is essential for them to be as pure as possible.

Influenza is a contagious viral disease affecting some 600 million people per year causing up to 500,000 deaths. Causative agents of the disease are enveloped viruses from the family of Orthomyxoviridae classified in three genera, influenza A, B, and C viruses. Increase of demand for the vaccine and threat of pandemic, together with some other disadvantages of traditional egg based vaccines, have stimulated development and introduction of new production strategies. Typically, downstream processes of influenza virus from allantoic fluids consist of clarification by centrifugation, concentration by ultra-filtration and purification by ultra-centrifugation. Early attempts of small-scale chromatographic purification of influenza virus on calcium phosphate and on agarose-gel columns were reported in the 1960s and 1970s. With the introduction of cell culture based processes, purification methods applying modern chromatography supports are being evaluated. Nayak et al. used a combination of depth filtration, inactivation, ultrafiltration and gel filtration to purify influenza virus derived from MDCK cells (Nayak D P. et al., J. Chromatogr. B Analyt Technol Biomed Life Sci, 2005; 823:75-81). Size exclusion chromatography was also used for purification of influenza A viruses in combination with anion exchange chromatography (Kalbfuss B. et al., Biotech Bioeng. 2007; 96:932-44). Chromatography supports with enhanced mass transfer, like membrane adsorbers and monoliths have been proved more efficient and were applied for purification of different viruses (Kramberger P. et al., J. Chromatogr. A 2007; 1144:143-9; Vicente T. et al., J. Memb. Sci., 2008; 311:270-83). Kalbfuss et al. compared strong and weak anion exchange membrane adsorbers for purification of influenza A viruses and achieved high virus recoveries up to 80% (Kalbfuss B. et al., J. Memb: Sci. 2007; 299:251-60). Affinity and pseudo affinity chromatography based on membrane adsorbers and monoliths was also studied for purification of influenza viruses (Opitz L. et al., Vaccine 2007; 25:939-47; Kalashnikova N. et al., Anal Chem 2008; 80:2188-98; Opitz L. et al., Biotechnol Bioeng 2009; 103:1144-54). All described methods were used for purification of inactivated influenza viruses and authors did not focus on preserving infectivity of the viruses.

Ye G J et al. report the use of benzonase treatment, clarification and column chromatography for the clearance of Herpes Simplex Virus (2015, URL:https:jiwww.agtc.comjuploadsjdocumentsJAGTC_Doc_5414_ASCOT_2015_Viral clearance_2015-04-21.pdf).

Zaveckas M. et al. report the purification of recombinant virus-like particles of porcine circovirus type 2 capsid protein with a purity of about 40% using SO3 monolith chromatography. Virus recovery was about 15% (J. Chromatogr. B: Biomedical Sciences & Applications, Elsevier, Amsterdam. vol. 991, 2015, pages 21-28).

Strauss D. et al. describe the use of anion exchange chromatography for viral removal (Biotechnol. Bioengineering, vol. 102, no. 1,2009, pages 168-175).

Ion exchange methacrylate monoliths for purification of replication deficient influenza viruses were used by Banjac M. et al. (Vaccine 2014; 32:2487-2492), however adsorption specifically for influenza B virus was low.

Thus there is a high and yet unmet demand on purification systems for viruses, specifically for influenza virus in high yield and with high purity.

Thus, there is also still a need for a fast, scalable, efficient and inexpensive downstream process to purify influenza viruses for vaccines or any other application requiring pure, immunogenic and/or infective virus.

SUMMARY OF THE INVENTION

It is the object of the present invention to provide improved purification methods for virus purification, specifically for influenza virus purification. It is a further object to develop a process for the purification of useful quantities of any influenza virus or its derivative, especially for vaccine or as viral vector use, either for laboratory or industrial scale needs, wherein the virus is immunogenic and/or has preserved infectivity.

The object is solved by the subject of the present invention.

The methods described here permit retrieval of purified infective virus particles, specifically infective influenza virus particles, at a high concentration in aqueous media. The methods are suitable for the preparation of laboratory or industrial quantities of any influenza virus particles, specifically of live virus.

The process of the invention is advantageous because due to the mild conditions the potency of the influenza virus, such as immunogenicity and/or infectivity can be substantially maintained.

According to the invention, there is provided a process for purifying virus particles, specifically influenza virus particles, from cell culture, comprising the steps in the indicated order:

a) subjecting the cell culture to centrifugation to get a supernatant fraction of virus particles, b) incubating said fraction with a nuclease, c) diluting the fraction with low conductivity buffer, d) subjecting said diluted fraction to a SO3 chromatography step, e) performing a washing step with low conductivity buffer, and f) eluting virus particles.

Specifically, the virus is an influenza virus, specifically selected from the group of influenza A, influenza B and influenza C virus. More specifically, the influenza virus is selected from the group consisting of influenza virus wild type, influenza virus containing modifications, including substitution mutations, insertions and/or deletions.

Specifically, the virus particles are diluted after elution.

According to a specific embodiment of the invention, an ultra filtration and/or a sterile filtration is performed after elution.

In a specific embodiment, the SO3 chromatography is a column chromatography, specifically methacrylate monolith column chromatography.

Specifically, the diluting buffer has a conductivity of 2 mS/cm or less.

Specifically, the washing buffer has a conductivity of about 12 mS/cm or less.

According to a specific embodiment, the buffer is selected from the group consisting of, Hepes, Tris, Tris base, potassium phosphate, sodium phosphate, Mops, Bis-Tris propane Bicine, Mes and Bis-Tris.

According to a specific embodiment, the washing buffer further contains one or more additives such as EDTA.

In a specific embodiment, the buffer further contains an osmotic stabilizer, specifically selected from sucrose, sorbitol and mannitol. Specifically, the buffer may contain 100 to 250 mM, specifically 150 to 200 mM, more specifically about 200 mM sucrose.

Specifically, the virus is eluted with a stepwise or linear gradient, specifically a salt gradient, more specifically a sodium chloride gradient.

In a specific embodiment, centrifugation is performed at a speed of at least 2,000 g, specifically at least 3,000 g, specifically at least 4,000 g, specifically at least 4,100 g. According to an embodiment, the centrifugation speed is in the range of about 2,000 g and 4,500 g.

According to an embodiment of the invention, the cell culture is performed with host cells, specifically with mammalian cells, more specifically Vero cells and MDCK cells are used.

In a specific embodiment, at least 50%, specifically at least 60%, specifically at least 70%, specifically at least 80%, specifically at least 85%, specifically at least 90%, specifically at least 95%, more specifically at least 99% host cell protein is removed.

In a specific embodiment, at least 50%, specifically at least 60%, specifically at least 70%, specifically at least 80%, specifically at least 85%, specifically at least 90%, specifically at least 95%, more specifically at least 99% of the host cell DNA is removed.

FIGURES

Figure 1B:
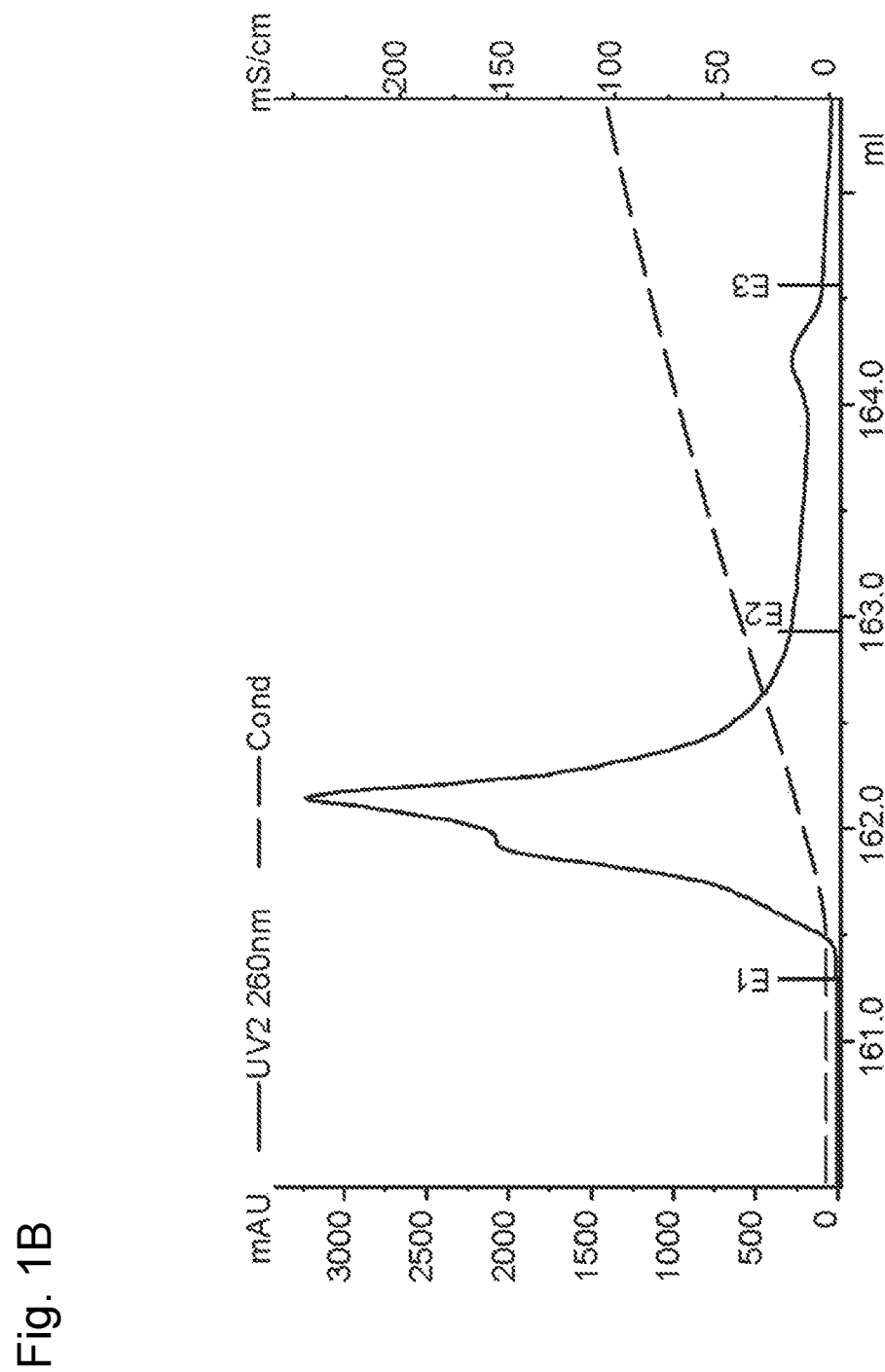

FIG. 1: Chromatogram of example 3. OD260 and conductivity are indicated by solid and dashed lines, respectively. Flow-through fractions (FT1 to FT4), wash fraction (WASH) and virus eluate fraction (E1) are indicated. a) overview, and b) detail of the virus eluate fraction.

Figure 2A:
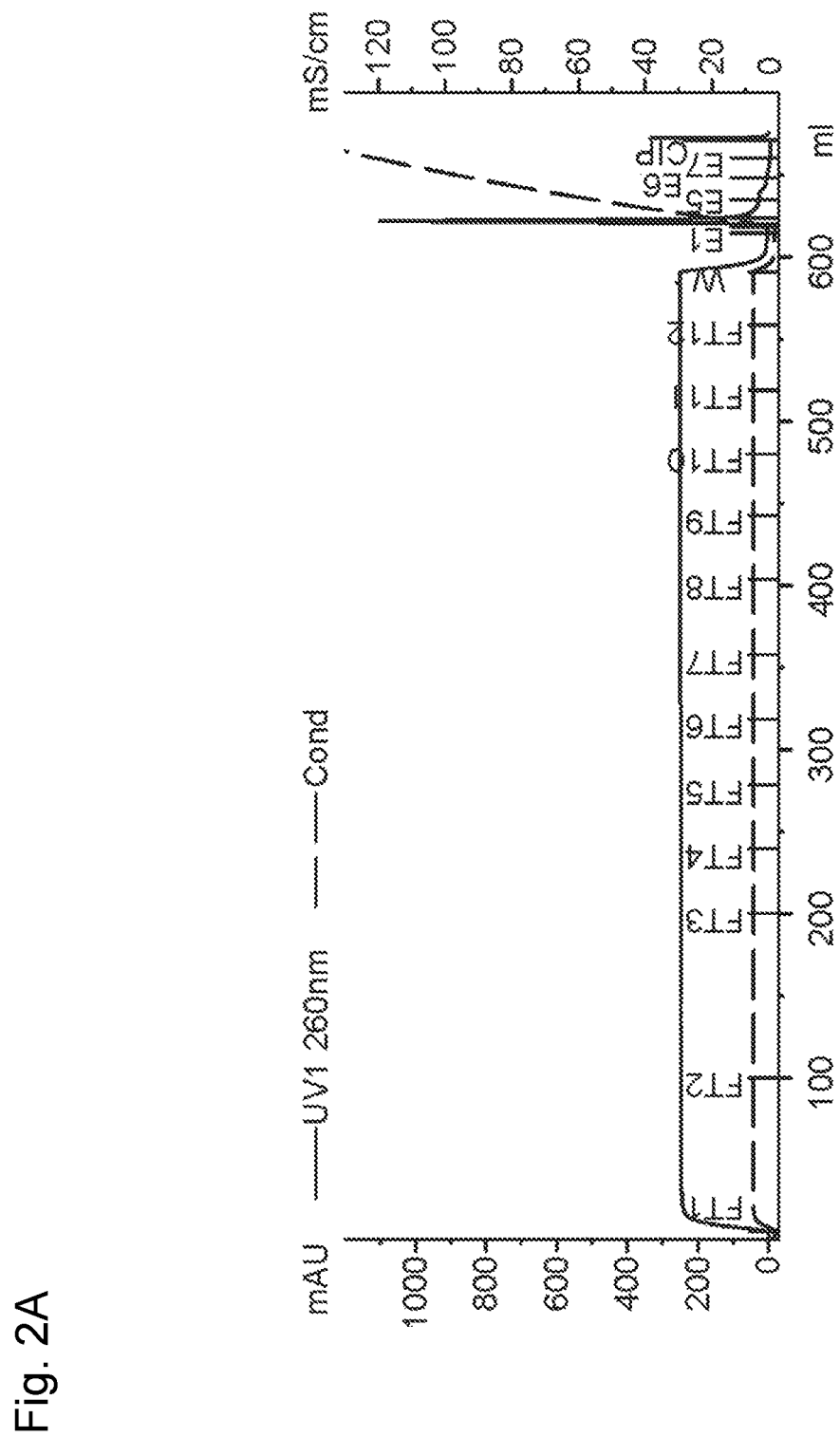
Figure 2B:
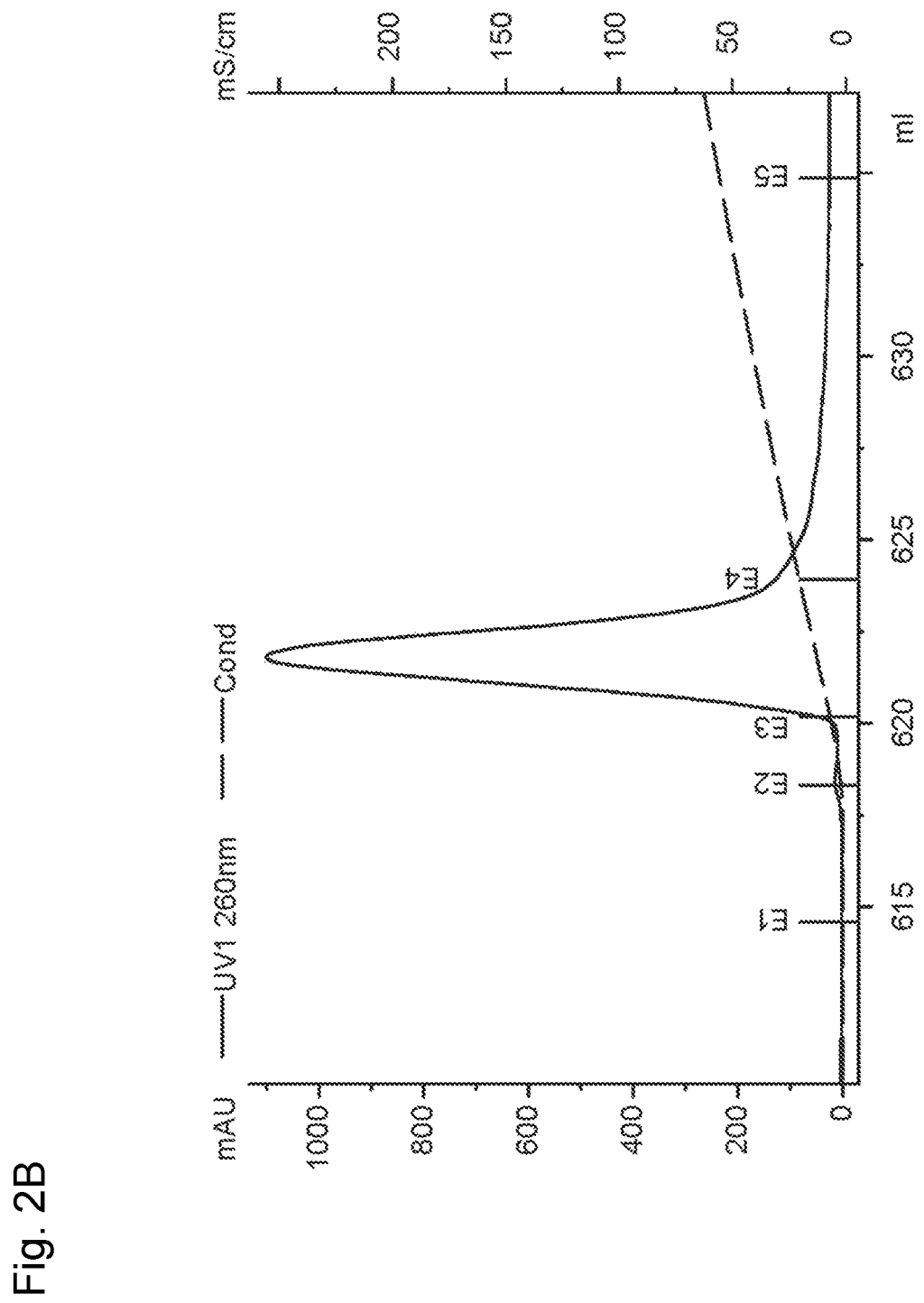

FIG. 2: Chromatogram of example 6. OD260 and conductivity are indicated by solid and dashed lines, respectively. Flow-through fractions (FT1 to FT12), wash fraction (W) and virus eluate fraction (E3) are indicated. a) overview, and b) detail of the virus eluate fraction.

DETAILED DESCRIPTION OF THE INVENTION

According to the invention, the term "about" encompasses the explicitly recited values as well as small deviations therefrom. Accordingly, a deviation from a recited value for 10%, preferably 5%, preferably 1% is encompassed by the term "about".

Any known upstream production process of influenza virus or its derivative can be used to generate the starting material for the purification process of the present invention.

Suitable sources of virus particles or derivatives thereof are any eukaryotic cells which support replication of the influenza virus. A preferred host cell is a mammalian host cell line which supports infection and replication of influenza virus.

Influenza virus can be propagated and prepared by any method known in the art. The virus can be cultured in chicken eggs or cell cultures according to known procedures explained in the literature. Preferably, influenza virus is harvested from virus-infected cells, for example Vero cells or MDCK cells. Cells may be infected at high multiplicity of infection in order to optimize yield. Any method suitable for recovering virus from infected cells may be used.

All viruses amenable for purification according to the inventive method shall be encompassed herein. The viruses may be enveloped viruses, specifically they are RNA viruses. The RNA viruses suitable for the purification according to the invention may be but are not limited to Orthomyxovirus, Flavivirus, Togavirus, Coronavirus, Hepatitis virus, Paramyxovirus, Rhabdovirus, Bunyavirus and Filovirus.

The influenza virus can be selected from the group of human influenza virus, avian influenza virus, equine influenza virus, swine influenza virus, feline influenza virus. Influenza virus is more particularly selected from strains A, B and C, preferably from strains A and B. Influenza strains may be derived from interpandemic (annual or seasonal) influenza strains. Alternatively, influenza virus particles may be derived from virus strains with the potential to cause a pandemic outbreak; i.e., influenza strains with new hemagglutinin compared to hemagglutinin in currently circulating strains, or influenza strains which are pathogenic in avian subjects and have the potential to be transmitted horizontally in the human population or influenza strains which are pathogenic to humans. Depending on the particular season and on the nature of the antigen included in the vaccine, the influenza antigens may be derived from one or more of the following hemagglutinin subtypes: H1, H2, H3, H4, H5, H6, H7, H8, H9, H10, H11, H12, H13, H14, H15 or H16. Preferably, the influenza virus or antigens thereof are from H1, H2, H3, H5, H7 or H9 subtypes. In one embodiment, the influenza viruses are from H2, H5, H6, H7 or H9 subtypes. In an alternative embodiment, the influenza viruses are from H1, H3 or B subtypes.

According to a specific embodiment, the influenza virus is an attenuated influenza virus. Specifically, the influenza virus comprises deletions or modifications within the pathogenicity factors inhibiting innate immune response of host cells. The attenuation can exemplarily be derived from cold-adapted virus strains or due to a deletion or modification within the NS1 gene (ΔNS1 virus) as described in WO99/64571 and WO99/64068, which are incorporated herein in total by reference.

Specifically, the influenza virus can be a virus vector comprising a truncated NS1 protein that contains up to 122 amino acids, preferably up to 121 amino acids, preferably up to 120 amino acids, preferably up to 119 amino acids, preferably up to 118 amino acids, preferably up to 117 amino acids, preferably up to 116 amino acids, preferably up to 115 amino acids, preferably up to 114 amino acids, preferably up to 113 amino acids, preferably up to 112 amino acids, preferably up to 111 amino acids, preferably up to 110 amino acids, preferably up to 109 amino acids, preferably up to 108 amino acids, preferably up to 107 amino acids, preferably up to 106 amino acids, preferably up to 105 amino acids, preferably up to 104 amino acids, preferably up to 103 amino acids, preferably up to 102 amino acids, preferably up to 101 amino acids, preferably up to 100 amino acids, preferably up to 99 amino acids, preferably up to 98 amino acids, preferably up to 97 amino acids, preferably up to 96 amino acids, preferably up to 95 amino acids, preferably up to 94 amino acids, preferably up to 93 amino acids, preferably up to 92 amino acids, preferably up to 91 amino acids, preferably up to 90 amino acids, preferably up to 89 amino acids, preferably up to 88 amino acids, preferably up to 87 amino acids, preferably up to 86 amino acids, preferably up to 85 amino acids, preferably up to 84 amino acids, preferably up to 83 amino acids, preferably up to 82 amino acids, preferably up to 81 amino acids, preferably up to 80 amino acids, preferably up to 79 amino acids, preferably up to 78 amino acids, preferably up to 77 amino acids, preferably up to 76 amino acids, preferably up to 75 amino acids, preferably up to 74 amino acids, preferably up to 73 amino acids of the N-terminus of the NS1 protein.

It was demonstrated that deletion of the NS1 protein leads to a significant attenuation of influenza virus due to lack of replication in interferon competent cells or organisms (replication deficient phenotype). Viruses lacking the NS1 protein are not able to antagonize cytokine production of infected cells, therefore inducing self-adjuvanting and immune modulating effects. The hallmark of immune response after immunization with DeINS1 virus is triggering of Th1 type of immune response associated with predominant IgG2A antibody isotype response (Ferko B. et al., J. Virol., 2004, 78(23): 13037-45).

"Modification" refers to a substitution or deletion of one or more nucleic acids as compared to a wild-type NS1 sequence. Modification within the NS gene can lead to virus particles that are growth deficient in interferon competent cells. Growth deficient means that these viruses are replication deficient as they undergo abortive replication in the respiratory tract of animals. Alternatively, the viruses can comprise deletion or modification of the PB1-F2 gene.

The method according to the invention can be specifically used for producing an influenza virus comprising a deletion of the NS1 protein functionality.

According to the invention derivatives of influenza virus are also encompassed, which are in particular genetically modified influenza viruses or virus-like particles or influenza virus particles (viral vectors) delivering foreign material, such as biologically or pharmaceutically active substances, e.g. biopolymers but also small molecules. Biopolymers are in particular proteins, such as antibodies, receptors enzymes; nucleic acids (antisense nucleic acids), lipids or polysaccharides.

Influenza virus-like particles can be generated e.g. from influenza virus proteins expressed in eukaryotic cells or by in vitro manipulation of influenza virus and/or molecules comprising influenza virus. Genetic manipulation of influenza virus genome may include mutations, deletions, insertions or any other manipulation of influenza virus genome. In particular the influenza virus particle contains at least one modification and/or deletion of the NS1 gene.

Influenza virus strains for use in vaccines change from season to season. Trivalent vaccines are typical, but higher valence, such as quadrivalence, is also contemplated in the present invention. The invention may use HA from pandemic strains (i.e. strains to which the vaccine recipient and the general human population are immunologically naive), and influenza vaccines for pandemic strains may be monovalent or may be based on a normal trivalent vaccine supplemented by a pandemic strain.

Compositions comprising virus particles produced according to the method of the invention may include antigen(s) from one or more influenza virus strains, including influenza A virus and/or influenza B virus. In particular, a trivalent vaccine including antigens from two influenza A virus strains and one influenza B virus strain is contemplated by the present invention. Alternatively, a quadrivalent vaccine including antigens from two influenza A virus strains and two influenza B virus strains is also within the scope of the present invention.

The compositions produced according to the invention are not restricted to monovalent compositions, i.e. including only one strain type, i.e. only seasonal strains or only pandemic strains. The invention also encompasses multivalent compositions comprising a combination of seasonal strains and/or of pandemic strains.

Once an influenza virus has been purified for a particular strain, it may be combined with viruses from other strains and/or with adjuvants known by the art.

The virus particles obtained by the methods described herein can be used for the preparation of compositions for treatment of individuals, specifically for prophylactic treatment, e.g. by vaccination.

The cell culture medium containing the virus particles is clarified by centrifugation as well known in the art. Specifically centrifugation is performed at about 4000 g, such as in the range of 2000 g and 4500 g, specifically in the range of 3500 g and 4500 g. Specifically, centrifugation is performed at about 2000 g, 2100 g, 2200 g, 2300 g, 2400 g, 2500 g, 2600 g, 2700 g, 2800 g, 2900 g, 3000 g, 3100 g, 3200 g, 3300 g, 3400 g, 3500 g, 3600 g, 3700 g, 3800 g, 3900 g, 4000 g, 4100 g, 4200 g, 4300 g, 4400 g, 4500 g or more.

Any nuclease or endonuclease may be used for incubating the virus particle containing supernatant fraction according to the invention. As examples, Cyanase™ or Benzonuclease® are well known industrially applicable nucleases. Cyanase™ is a cloned highly active non-Serratia based non-specific endonuclease that degrades single and double stranded DNA and RNA. Benzonase® or Supernuclease as used herein is a nuclease, specifically an endonuclease from *Serratia marcescens*. The protein is a dimer of 30 kDa subunits with two essential disulfide bonds. This endonuclease attacks and degrades all forms of DNA and RNA (single stranded, double stranded, linear and circular) and is effective over a wide range of operating conditions. The optimum pH for enzyme activity is found to be 8.0-9.2. It completely digests nucleic acids to 5'-monophosphate terminated oligonucleotides 3 to 5 bases in length.

Benzonase® unit definition is as follows: One unit will digest sonicated salmon sperm DNA to acid-soluble oligonucleotides equivalent to a $\Delta A_{260}$ of 1.0 in 30 min at pH 8.0 at 37 C (reaction volume 2.625 ml).

The nuclease as used herein may be added to the virus containing host cell supernatant at a final concentration in the range of 10 and 50 U/ml, specifically 15 and 40 U/ml, specifically at about 20 U/ml.

According to a specific embodiment, the nuclease-treated harvest is diluted with buffer at a ratio from 9:1 to 1:5.

Performing the purification process under low conductivity conditions is crucial for the invention. Therefore, diluting the virus particle fraction with a low conductivity buffer and performing a washing step under low conductivity conditions are performed within the purification method of the invention. Although low conductivity may further be obtained by diluting the fraction, excessive dilution can result in stress increase and decreased viability of the virus particles. More preferred is the use of a low conductivity buffer.

According to a specific embodiment, the low conductivity buffers are combined with compounds that decrease the osmotic stress to the virus particles. Said compounds may be, but are not limited to sucrose, sorbitol and mannitol, or glucose.

"Conductivity value" refers to ability of an electrolyte solution to conduct electricity. The conductivity of a solution of an electrolyte can be measured by, for example, determining the resistance of the solution between two electrodes separated by a fixed distance. Conductivity values are expressed as milliSiemens per cm (mS/cm).

Conductivity can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the buffers is modified to achieve the desired conductivity.

The term "low conductivity buffer" denotes an aqueous solution with a low conductivity value.

The conductivity value may be about 5 mS/cm or less with respect to the buffer used for dilution (low conductivity dilution buffer). In some embodiments of any of the methods described herein, the dilution buffer has a conductivity in the range of about 0.5 to 5 mS/cm, specifically of about 0.5 to 5 mS/cm, specifically of about 0.1 mS/cm, 0.2 mS/cm, 0.3 mS/cm, 0.4 mS/cm, 0.5 mS/cm, 0.6 mS/cm, 0.7 mS/cm, 0.8 mS/cm, 0.9 mS/cm, 1.0 mS/cm, 1.5 mS/cm, 2.0 mS/cm, 3.0 mS/cm, 4.0 mS/cm, 5 mS/cm.

The conductivity value for the washing buffer (low conductivity wash buffer) may be higher, specifically between 0.5 and 12 mS/cm, specifically between 1 and 10 mS. In some embodiments of any of the methods described herein, the washing buffer has a conductivity of about 0.5 mS/cm, 1.0 mS/cm, 1.2 mS/cm, 1.5 SmS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm 9.0 mS/cm, 9.5 mS/cm, 10 mS/cm, 10.5 mS/cm, 11.0 mS/cm, 11.5 mS/cm or 12.0 mS/cm.

In a specific embodiment the wash buffer further comprises one or more additives such as but not limited to EDTA. Specifically, EDTA is present in a concentration of 0.1 to 50 mM, specifically in a concentration of 10 to 30 mM, specifically in a concentration of about 20 mM.

According to a specific embodiment, the conductivity value of the whole virus fraction subjected to chromatography has maximum conductivity of 12 mS/cm, more specifically said fraction is in the range of about 0.5 to 12 mS/cm, specifically of about 1.5 to 10 mS/cm, more specifically 2 to 8, more specifically 4 to 7, more specifically 2 to 4 mS/cm.

With regard to purification of influenza A virus, according to a specific embodiment, conductivity of the dilution buffer is in in the range of 0.5 to 8 mS/cm, conductivity of the virus particle fraction subjected to chromatography, i.e. the virus load, specifically is in the range of 0.5 to 12 mS/cm, specifically in the range of 1 to 9.5 mS/cm specifically in the range of 1 to 8 mS/cm.

With regard to purification of influenza B virus, according to a specific embodiment, conductivity of the dilution buffer is in in the range of 0.5 to 2 mS/cm, conductivity of the virus particle fraction subjected to chromatography, i.e. the virus load, specifically is in the range of about 0.5 to 12 mS/cm, specifically of about 1 to 7 mS/cm.

The respective conductivity applicable in the process described herein shall permit efficient binding of the virus particles to the chromatographic material. The respective conductivity can be evaluated by the skilled person, for example by using a TCID50 or fluorescent focus assay (FFA) for determining the virus flow-through and SO3 virus eluate.

It is determined according to the present invention that in case 10% or more, specifically 3% or more, specifically 2% or more, specifically 1% or more are found in the flow-through fraction of the chromatography, conductivity is considered to be too high for efficient virus binding according to the method of the invention.

In a specific embodiment for purifying influenza A virus the virus particle fraction subjected to chromatography in the presence of the low conductivity dilution buffer (the virus load) has a conductivity in the range of 5 to 9.5 mS/cm, specifically 5 to 9 mS/cm, and the washing buffer has a conductivity in the range of about 0.5. to 9 mS/cm.

In a specific embodiment for purifying influenza B virus the virus particle fraction (the virus load) subjected to chromatography in the presence of the low conductivity dilution buffer (the virus load) has a conductivity in the range of 5 to 9 mS/cm, and the washing buffer has a conductivity in the range of about 0.5-8 mS/cm, specifically of about 0.5 to 7 mS/cm.

In a specific embodiment for purifying viruses, specifically of influenza viruses, ethylenediamine-tetraacetic acid (EDTA) is added to the SO3 wash buffer, as an example, but not limited to, at a concentration of 0.5-20 mM.

Aqueous solution of low conductivity" may encompass, as an example, a 10 to 100 mM Hepes buffer containing 200 mM sucrose.

SO3 (sulfonate) is a strong cation exchange group, fully charged between pH 2-13. It selectively binds molecules with a predominant positive charge over a working pH range of 2-13. For the chromatographic material used in the method of the invention, SO3 (sulfonyl) functional groups are attached to any suitable resin.

Preferably, a monolithic support based on poly(glycidyl methacrylate-co-ethylene dimethacrylate) matrix, with sulfonate functional groups (e.g. CIM® SO3 monolithic column) is used in the SO3 cation exchange chromatography step of the process of the present invention. Monolithic SO3 chromatography is specifically used as described herein for purification and concentration of viruses that bind to the ion exchanger on the basis of their positive charge.

Preferably, the chromatography material is equilibrated with low conductivity buffer as described herein. Specifically, said low conductivity buffer for equilibration has a conductivity in the range of 0.5 mS/cm to 2 mS/cm.

Elution of the virus particle fraction can be performed either gradually or stepwise. According to the invention, buffer containing any salt can be used for eluting the virus. Specifically, NaCl is used herein. Specifically the salt can be at a concentration of up to 2M, specifically up to 1.5M, 1 M, 0.9M, 0.8M, 0.7M, 0.6M, 0.5M, 0.4M, 0.3M, 0.2M. To preserve infectivity of the virus, incubation time at high salt concentration shall be limited.

Compared to Banjac et al. (2014) reducing the conductivity of influenza A H1N1 virus harvest significantly increased the dynamic binding capacity of the SO3 monolith from approximately 9 log 10 infectious virus particles per ml SO3 column volume to 10.5 log 10 infectious virus particles per ml SO3 column volume (i.e. 30-fold). For influenza B virus reducing the conductivity of the harvest also resulted in a dynamic binding capacity of 10.5 log 10 infectious virus particles per ml SO3 column volume. Since Banjac et al. did not reduce the conductivity of the influenza B virus harvest before loading to the SO3 column a significant amount of virus (37.1%) was found in the flow through. The dynamic binding capacity for influenza B was therefore not determined by Banjac et al.

As an additional step sterile filtration or ultrafiltration may be performed to further eliminate bioburden. Therefore the eluate may be filtered through a 0.22 μm filter. The filter may be constructed from various materials, which may include but are not limited to polypropylene, cellulose, cellulose esters, nylon, polyethersulfone, or any other material which is consistent with low unspecific influenza virus binding. The filter may have a single membrane layer or more than one layer or may incorporate a prefilter of the same or different material.

The filtrated influenza virus can be held frozen or kept at approximately 4° C. for subsequent manipulation.

The invention encompasses following items:

1. Process for purifying virus particles from cell culture, comprising the steps in the indicated order:
   a) subjecting the cell culture to centrifugation to get a supernatant fraction of virus particles,
   b) incubating said fraction with a nuclease,
   c) diluting the fraction with low conductivity dilution buffer,
   d) subjecting said diluted fraction to a SO3 chromatography step, under conditions allowing efficient virus binding,
   e) performing a washing step with low conductivity wash buffer, and
   f) eluting virus particles.

2. The process of item 1, wherein the virus is an influenza virus.

3. The process of item 1 or 2, wherein the virus particles are diluted after elution.

4. The process according to any one of items 1 to 3, wherein an ultra and/or sterile filtration is performed after elution.

5. The process according to any one of items 1 to 4, wherein the SO3 chromatography is a column chromatography, specifically methacrylate monolith column.

6. The process according to any one of items 1 to 5, wherein the dilution buffer has a conductivity of 5 mS/cm or less, specifically of 1 mS or less.

7. The process according to any one of items 1 to 6, wherein the wash buffer has a conductivity of 12 mS/cm or less, specifically of 7 mS or less.

8. The process according to any one of items 1 to 7, wherein the wash buffer further contains one or more additives, specifically EDTA.

9. The process according to any one of items 1 to 8, wherein the buffer is selected from the group consisting of Hepes, Tris, Tris base, potassium phosphate, sodium phosphate, Mops, Bis-Tris propane Bicine, Mes and Bis-Tris, 10. The process according to any one of items 1 to 9, wherein the buffer further contains sucrose, sorbitol and/or mannitol.

11. The process according to any one of items 1 to 10, wherein virus is eluted with a stepwise or linear gradient, specifically a sodium chloride gradient.

12. The process according to any one of items 1 to 11, wherein the virus is influenza virus, specifically selected from the group consisting of influenza A, influenza B and influenza C virus.

13. The process according to any one of items 1 to 12, wherein the influenza virus is selected from the group consisting of influenza virus wild type, influenza virus containing modifications, including substitution mutations, insertions and/or deletions.

14. The process according to any one of items 1 to 13, wherein centrifugation speed is at least 2,000 g, specifically at least 3,000 g, specifically at least 4,000 g, specifically at least 4,100 g.

15. The process according to any one of items 1 to 14, wherein cell culture is performed with host cells.

16. The process according to any one of items 1 to 15, wherein at least 50%, specifically at least 60%, specifically at least 70%, specifically at least 80%, specifically at least 85%, specifically at least 90%, specifically at least 95%, more specifically at least 99% host cell protein is removed.

17. The process according to any one of items 1 to 16, wherein at least 50%, specifically at least 60%, specifically at least 70%, specifically at least 80%, specifically at least 85%, specifically at least 90%, specifically at least 95%, more specifically at least 99% of the host cell DNA is removed.

18. The process according to any one of items 1 to 17, wherein the host cells are mammalian cells, specifically Vero cells.

The present invention is further illustrated by the following examples without being limited thereto.

EXAMPLES

Influenza a Virus Purification:

Example 1: Undiluted H1N1 Virus

Influenza A H1N1 NS106-E6E7 virus was grown in Vero cells seeded in cell factories. Influenza A H1N1 NS106-E6E7 virus is a derivative of IVR-116 that lacks the C-terminal 124 amino acids of the NS1 open reading frame and therefore only expresses the N-terminal 106 amino acids of NS1. The E6 and E7 proteins of the human papillomavirus 16 (HPV16) were fused in frame to the C-terminus of the NS106 protein via a 2A sequence. The virus harvest was clarified by centrifugation for 30 min at 4.100 g and 22° C. The clarified harvest was treated with Benzonase (20 U/ml) in the presence of 2 mM Mg2+ for 2 h at RT.

97 ml Benzonase-treated harvest (HCB) with a conductivity of 13 mS/cm was loaded on a 1 ml monolithic CIM SO3 column previously equilibrated with buffer 50 mM HEPES, 200 mM sucrose, pH 7.5. After washing with 50 mM HEPES, 200 mM sucrose, pH 7.5 the virus was eluted in 50 mM Hepes pH 7.5, 400 mM NaCl, 200 mM sucrose (step gradient).

Infectious titers in HCB, SO3 wash, SO3 flow-through, and SO3 eluate were determined by TCID50 assay. While 65% infectious virus was found in the eluate fraction 8% virus was detected in the flow-through, indicating that the conductivity of the HCB was too high to permit efficient virus binding to the SO3 column.

Example 2: 1:1 Diluted Virus

Influenza A H1N1 NS106-E6E7 virus was grown in Vero cells seeded in cell factories. The virus harvest was clarified by centrifugation for 30 min at 4.100 g and 22° C. The clarified harvest was treated with Benzonase (20 U/ml) in the presence of 2 mM Mg2+ for 2 h at RT.

50 ml HCB (conductivity 13 mS/cm) was diluted with 50 ml 50 mM Hepes, 200 mM sucrose, pH 7.0 (conductivity 700 μS/cm) resulting in a conductivity of 7.05 mS/cm and loaded on a 1 ml monolithic CIM SO3 column previously equilibrated with buffer 50 mM HEPES, 200 mM sucrose, pH 7.5. After washing with 50 mM HEPES, 200 mM sucrose, pH 7.5 (conductivity 1.2 mS/cm) the virus was eluted with a linear NaCl gradient (up to 2M NaCl) in 50 mM Hepes pH 7.5, 200 mM sucrose. Infectious titers in HCB, diluted HCB (SO3 load), SO3 wash, SO3 flow-through, and SO3 eluate were determined by TCID50 assay. In contrast to the previous experiment no virus was detected in the flow-through while 67% virus was found in the eluate fraction indicating that the conductivity in the load was low enough for efficient virus binding to the SO3 column.

Example 3: 2:1 Diluted Virus

Influenza A H1N1 NS106-E6E7 virus was grown in Vero cells seeded in cell factories. The virus harvest was clarified by centrifugation for 30 min at 4,100 g and 22° C. The clarified harvest was treated with Benzonase (20 U/ml) in the presence of 2 mM Mg2+ for 2 h at RT.

100 ml HCB (conductivity 13 mS/cm) was diluted with 50 ml 50 mM Hepes, 200 mM sucrose, pH 7.0 (conductivity 700 μS/cm) resulting in a conductivity of 9.2 mS/cm and loaded on a 0.1 ml monolithic CIM SO3 column previously equilibrated with buffer 50 mM HEPES, 200 mM sucrose, pH 7.0. After washing with 50 mM HEPES, 200 mM sucrose, pH 7.5 (conductivity 1.2 mS/cm) the virus was eluted with a linear NaCl gradient (up to 2M NaCl) in 50 mM Hepes pH 7.5, 200 mM sucrose (FIG. 1). Infectious titers in HCB, diluted HCB (SO3 load), SO3 wash, SO3 flow-through, and SO3 eluate were determined by FFA (fluorescent focus assay). Only 1.5% infectious virus was found in the flow-through while 73% infectious virus was recovered in the eluate.

The dynamic binding capacity was calculated to be 10.5 log 10 FFU/ml SO3 column volume. Said binding capacity is 1.5 log 10 more, thus 30 fold higher than described by Bajac et al. (2014).

Influenza B Virus Purification:

Example 4

Influenza B NS106-E6E7 virus was grown in Vero cells seeded in cell factories. Influenza B NS106-E6E7 virus is a derivative of B/Thueringen/02/06 that lacks the C-terminal 175 amino acids of the NS1 open reading frame and therefore only expresses the N-terminal 106 amino acids of NS1. The E6 and E7 proteins of the human papillomavirus 16 (HPV16) were fused in frame to the C-terminus of the NS106 protein via 2A sequence. The virus harvest was clarified by centrifugation for 30 min at 4,100 g and 22° C. The clarified harvest was treated with Benzonase (20 U/ml) in the presence of 2 mM Mg2+ for 2 h at RT.

48 ml HCB (conductivity 13.4 mS/cm) was loaded on a 1 ml monolithic CIM SO3 column previously equilibrated with buffer 50 mM HEPES, 200 mM sucrose, pH 7.0 (conductivity 700 μS/cm). After washing with 50 mM HEPES, 200 mM sucrose, pH 7.5 (conductivity 1.2 mS/cm) the virus was eluted with a linear NaCl gradient (up to 2M NaCl) in 50 mM Hepes pH 7.5, 200 mM sucrose.

Infectious titers in HCB, SO3 wash, SO3 flow-through, and SO3 eluate were determined by TCID50 assay. 60% infectious virus was found in the flow-through and only 34% infectious virus was recovered in the eluate fraction, indicating that the conductivity of the HCB was too high to permit efficient virus binding to the SO3 column.

Example 5

Influenza B NS106-E6E7 virus was grown in Vero cells seeded in cell factories. The virus harvest was clarified by centrifugation for 30 min at 4,100 g and 22° C. The clarified harvest was treated with Benzonase (20 U/ml) in the presence of 2 mM Mg2+ for 2 h at RT.

50 ml HCB (conductivity 13.4 mS/cm) was diluted with 50 ml 50 mM Hepes, 200 mM sucrose, pH 7.0 (conductivity 700 μS/cm), resulting in a conductivity of 7.04 mS/cm, and was loaded on a 1 ml monolithic CIM SO3 column previously equilibrated with buffer 50 mM HEPES, 200 mM sucrose, pH 7.0. After washing with 50 mM HEPES, 200 mM sucrose, pH 7.5 (conductivity 1.2 mS/cm) the virus was eluted with a linear NaCl gradient (up to 2M NaCl) in 50 mM Hepes pH 7.5, 200 mM sucrose.

Infectious titers in HCB, diluted HCB (SO3 load), SO3 wash, SO3 flow-through, and SO3 eluate were determined by TCID50 assay. Less than 0.1% infectious virus was found in the flow-through while 84.5% infectious virus was recovered in the eluate fraction, indicating that the conductivity of the load was low enough for efficient virus binding to the SO3 column.

Example 6

Influenza B NS106-E6E7 virus was grown in Vero cells seeded in cell factories. The virus harvest was clarified by centrifugation for 30 min at 4.100 g and 22° C. The clarified harvest was treated with Benzonase (20 U/ml) in the presence of 2 mM Mg2+ for 2 h at RT.

300 ml HCB (conductivity 13.4 mS/cm) was diluted with 300 ml 50 mM Hepes, 200 mM sucrose, pH 7.0 (conductivity 700 μS/cm), resulting in a conductivity of 7.6 mS/cm, and was loaded on a 1 ml monolithic CIM SO3 column previously equilibrated with buffer 50 mM HEPES, 200 mM sucrose, pH 7.0. After washing with 50 mM HEPES, 200 mM sucrose, pH 7.5 (conductivity 1.2 mS/cm) the virus was eluted with a linear NaCl gradient (up to 2M NaCl) in 50 mM Hepes pH 7.5, 200 mM sucrose (FIG. 2).

Infectious titers in HCB, diluted HCB (SO3 load), SO3 flow-through, SO3 wash, and SO3 eluate were determined by FFA assay. Only 0.12% infectious virus was found in the flow-through while 80.6% infectious virus was recovered in the eluate fraction, confirming that the conductivity of the load was low enough to permit efficient virus binding to the SO3 column.

The dynamic binding capacity was calculated to be 10.5 log 10 FFU/ml SO3 column volume.

Example 7

Determination of maximum conductivity for efficient virus binding to the SO3 column.

Influenza A or B virus is grown in Vero cells seeded in cell factories. The virus harvest is clarified by centrifugation for 30 min at 4,100 g and 22° C. The clarified harvest is treated with Benzonase (20 U/ml) in the presence of 2 mM Mg2+ for 2 h at RT. The conductivity of the HCB usually will be in the range of 14 mS/cm.

10 ml HCB containing a maximum of 9 log 10 TCID50 are diluted with 1.7 ml 50 mM Hepes pH 7.0, 200 mM sucrose (resulting in a conductivity of approximately 12 mS/cm) and loaded on a 1 ml monolithic CIM SO3 column previously equilibrated with buffer 50 mM HEPES, 200 mM sucrose, pH 7.0. After washing with 50 mM HEPES, 200 mM sucrose, pH 7.5 (conductivity 1.2 mS/cm) the virus is eluted with a linear NaCl gradient in 50 mM Hepes pH 7.5, 200 mM sucrose.

Infectious titers in diluted HCB (=SO3 load), SO3 wash, flow-through and SO3 eluate are determined by e.g. TCID50 or FFA assay. If more than 1% infectious virus is found in the flow-through, the conductivity is considered to be too high for efficient virus binding. The conductivity of the SO3 load therefore has to be lowered gradually until less than 1% virus is found in the flow-through.

Example 8

Influenza B NS106-E6E7 virus was grown in Vero cells seeded in cell factories. The virus harvest was clarified by centrifugation for 30 min at 4.100 g and 22° C. The clarified harvest was treated with Benzonase® (20 U/ml) in the presence of 2 mM Mg2+ for 2 h at RT.

14.500 ml HCB (conductivity 13.7 mS/cm) was diluted with 14.500 ml 50 mM Hepes, 200 mM sucrose, pH 7.0 (conductivity 630 µS/cm), resulting in a conductivity of 7.2 mS/cm, and was loaded on a 80 ml monolithic CIM SO3 column previously conditioned using 50 mM HEPES 200 mM sucrose pH 7.0 (+2 M NaCl) and equilibrated with 50 mM HEPES 200 mM sucrose pH 7.0. After loading and washing with 50 mM HEPES, 200 mM sucrose, 50 mM NaCl, pH 7.5 (conductivity 5.0 mS/cm), the virus was eluted with a linear NaCl gradient (up to 2M NaCl) in 50 mM Hepes 200 mM sucrose pH 7.5. Infectious titers were determined by FFA assay. Vero host cell protein content and residual Vero cell DNA were analysed by ELISA and qPCR, respectively.

Infectious virus recovery was 83.4%. Host cell protein was depleted by 99.7% and host cell DNA by more than 99.99%. The dynamic binding capacity was calculated to be 10.8 log 10 FFU/ml SO3 column volume.

Example 9

Influenza B NS106-E6E7 virus was grown in Vero cells seeded in cell factories. The virus harvest was clarified by centrifugation for 30 min at 4.100 g and 22° C. The clarified harvest was treated with Benzonase® (20 U/ml) in the presence of 2 mM Mg2+ for 2 h at RT.

95 ml HCB (conductivity 14.5 mS/cm) was diluted with 95 ml 50 mM Hepes, 200 mM sucrose, pH 7.0 (conductivity 700 µS/cm), resulting in a conductivity of 7.6 mS/cm, and was loaded on a 1 ml monolithic CIM SO3 column previously conditioned using 50 mM HEPES 200 mM sucrose pH 7.0 (+2 M NaCl) and equilibrated with 50 mM HEPES 200 mM sucrose pH 7.0. After loading the column was washed with 50 mM HEPES, 200 mM sucrose, 50 mM NaCl, pH 7.5 (conductivity 6.3 mS/cm). The virus was eluted with a linear NaCl gradient (up to 2M NaCl) in 50 mM Hepes 200 mM sucrose pH 7.5. Infectious titers were determined by FFA assay. Benzonase® content was analysed by ELISA.

Virus recovery in the eluate fraction was 78%. 99.48% Benzonase® was depleted at eluate level. This corresponds to 7.7 ng Benzonase per 10 log 10 infectious virus.

Example 10

Influenza B NS106-E6E7 virus was grown in Vero cells seeded in cell factories. The virus harvest was clarified by centrifugation for 30 min at 4.100 g and 22° C. The clarified harvest was treated with Benzonase (20 U/ml) in the presence of 2 mM Mg2+ for 2 h at RT.

95 ml HCB (conductivity 14.5 mS/cm) was diluted with 95 ml 50 mM Hepes, 200 mM sucrose, pH 7.0 (conductivity 700 µS/cm), resulting in a conductivity of 7.7 mS/cm, and was loaded on a 1 ml monolithic CIM SO3 column previously conditioned using 50 mM HEPES 200 mM sucrose pH 7.0 (+2 M NaCl) and equilibrated with 50 mM HEPES 200 mM sucrose pH 7.0. After loading, the column was washed with 50 mM HEPES, 200 mM sucrose, 20 mM EDTA, pH 7.5 (conductivity 5.1 mS/cm) and with 50 mM HEPES, 200 mM sucrose, pH 7.5. The virus was eluted with a linear NaCl gradient (up to 2M NaCl) in 50 mM Hepes 200 mM sucrose pH 7.5. Infectious titers were determined by FFA assay. Benzonase® content was analysed by ELISA.

Virus recovery in the eluate fraction was 90%. 99.99% Benzonase® was depleted at eluate level. This corresponds to 0.3 ng Benzonase® per 10 log 10 infectious virus. Compared to example 9, Benzonase® content in the virus eluate was therefore reduced by another 96%.

Example 11

15000 Units of Benzonase® in 10 mL OptiPro diluted with 5 mL 50 mM HEPES 200 mM sucrose pH 7.0 was loaded on a preconditioned and equilibrated 0.1 ml monolithic SO3 column. After loading, the column was washed with either 50 mM HEPES, 200 mM sucrose, 75 mM NaCl, pH 7.5 or 50 mM HEPES 200 mM sucrose 20 mM EDTA pH 7.5 followed by 50 mM HEPES, 200 mM sucrose, pH 7.5. Elution was done with a linear NaCl gradient (up to 2M NaCl) in 50 mM Hepes 200 mM sucrose pH 7.5. Load, washes and eluate fractions were analysed for Benzonase® content by SDS PAGE and silver staining. When column washing was performed with 75 mM NaCl, Benzonase® was still detectable in the eluate. In contrast, following washing with 20 mM EDTA no Benzonase® was found in the eluate, confirming the results from example 10.

The invention claimed is:

1. A process for purifying virus particles from cell culture, comprising the steps in the following order:
   a) subjecting the cell culture to centrifugation to obtain a supernatant fraction of virus particles,
   b) incubating the supernatant fraction with a nuclease,
   c) diluting the supernatant fraction with a low conductivity dilution buffer to obtain a diluted fraction,
   d) subjecting the diluted fraction to a SO3 chromatography step,
   e) performing a washing step with low conductivity wash buffer, wherein the wash buffer has a conductivity of 12 mS/cm or less, and
   f) eluting virus particles.

2. The process of claim 1, wherein the virus is an influenza virus.

3. The process of claim 1, wherein the virus particles are diluted after elution.

4. The process according to claim 1, wherein an ultra and/or sterile filtration is performed after elution.

5. The process according to claim 1, wherein the SO3 chromatography step is a column chromatography step.

6. The process according to claim 1, wherein the dilution buffer has a conductivity of 5 mS/cm or less.

7. The process according to claim 1, wherein the wash buffer further contains EDTA.

8. The process according to claim 1, wherein the dilution buffer or the wash buffer comprises a component selected from the group consisting of Hepes, Tris, Tris base, potassium phosphate, sodium phosphate, Mops, Bis-Tris propane Bicine, Mes and Bis-Tris.

9. The process according to claim 1, wherein the dilution buffer or the wash buffer further contains sucrose, sorbitol and/or mannitol.

10. The process according to claim 1, wherein virus is eluted with a stepwise elution or linear gradient elution.

11. The process according to claim 2, wherein the influenza virus is selected from the group consisting of influenza A, influenza B and influenza C virus.

12. The process according to claim 11, wherein the influenza virus is selected from the group consisting of a wild type influenza virus and an influenza virus containing modifications, wherein the modifications comprise substitution mutations, insertions and/or deletions.

13. The process according to claim 1, wherein centrifugation is performed at a speed of is least 2,000 g, at least 3,000 g, at least 4,000 g, or at least 4,100 g.

14. The process according to claim 1, wherein cell culture is performed with Vero cells.

15. The process according to claim 1, wherein at least 50%, at least 60%, at least 70%, at least 80%, at least 85%, at least 90%, at least 95%, or at least 99% of cell protein is removed.

16. The process according to claim 1, wherein at least 50%, at least 60%, at least 70%, at least 80%, at least 85%, at least 90%, at least 95%, or at least 99% of cell DNA is removed.

17. The process according to claim 5, wherein the column chromatography step is performed with a methacrylate monolith column.

18. The process according to claim 6, wherein the dilution buffer has a conductivity of 1 mS/cm or less.

19. The process according to claim 10, wherein the linear gradient elution is a sodium chloride gradient elution.

* * * * *